United States Patent [19]

Miller

[11] 4,423,269
[45] Dec. 27, 1983

[54] OLIGOMERIZATION OF GASEOUS OLEFINS

[75] Inventor: Stephen J. Miller, San Francisco, Calif.

[73] Assignee: Chevron Research Company, San Francisco, Calif.

[21] Appl. No.: 305,680

[22] Filed: Sep. 25, 1981

[51] Int. Cl.³ .............................................. C07C 2/02
[52] U.S. Cl. ................................... 585/533; 585/510; 585/530
[58] Field of Search ................ 585/517, 530, 533, 510

[56] References Cited

U.S. PATENT DOCUMENTS

| | | | |
|---|---|---|---|
| 3,325,465 | 6/1967 | Jones et al. | 260/94.9 |
| 3,756,942 | 9/1973 | Cattanach | 208/137 |
| 3,827,968 | 8/1974 | Givens et al. | 208/49 |
| 3,960,978 | 6/1976 | Givens | 585/531 |
| 4,211,640 | 7/1980 | Garwood et al. | 208/255 |
| 4,227,992 | 10/1980 | Garwood et al. | 208/46 |
| 4,238,318 | 12/1980 | Kouwenhoven et al. | 208/137 |
| 4,289,607 | 9/1981 | Kokotailo | 585/533 |
| 4,324,940 | 4/1982 | Dessau | 585/533 |

*Primary Examiner*—Curtis R. Davis
*Attorney, Agent, or Firm*—D. A. Newell; S. R. La Paglia; W. L. Stumpf

[57] ABSTRACT

A process for oligomerizing gaseous olefins using intermediate pore size molecular sieves is disclosed.

22 Claims, 4 Drawing Figures

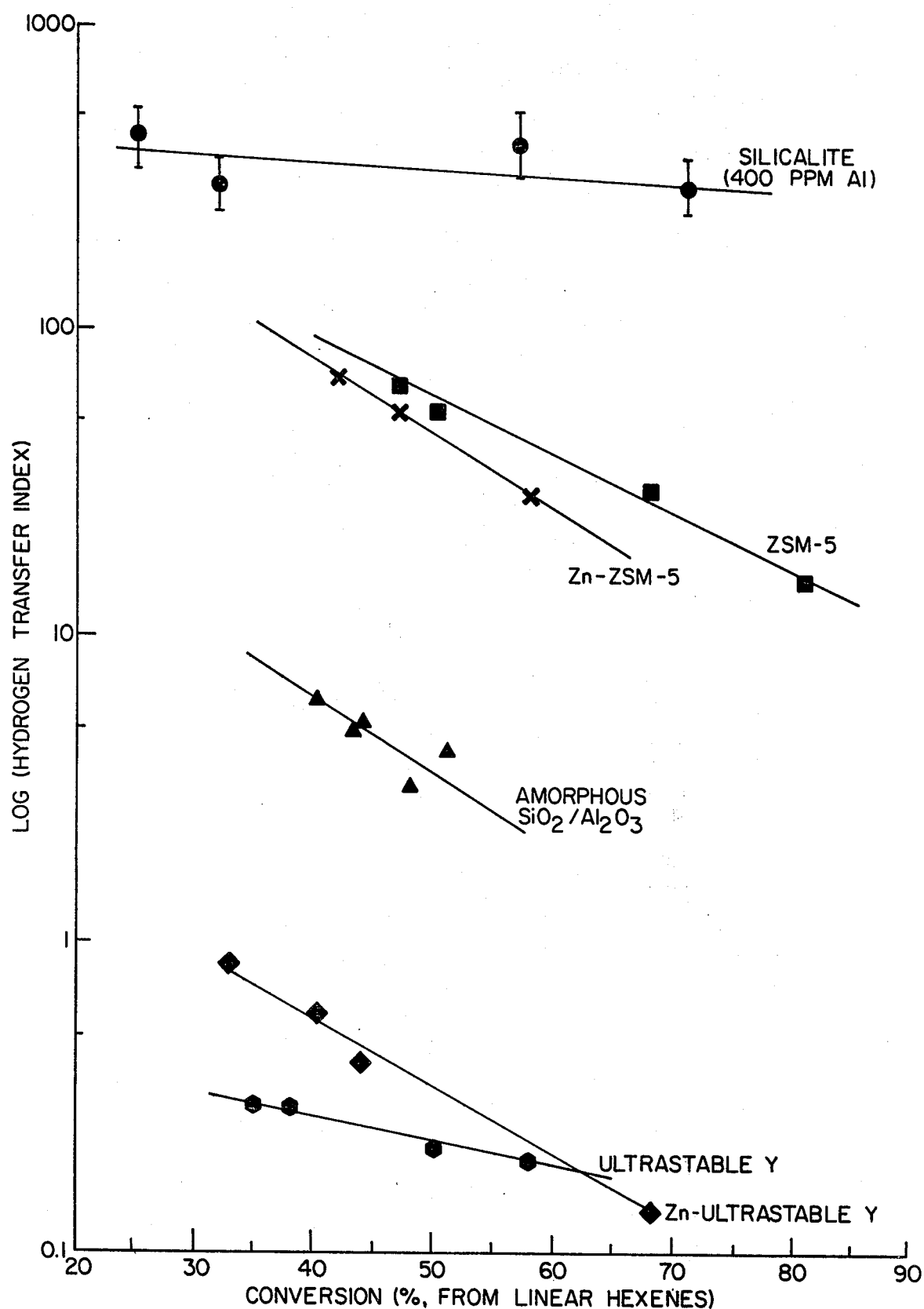
FIG._1.

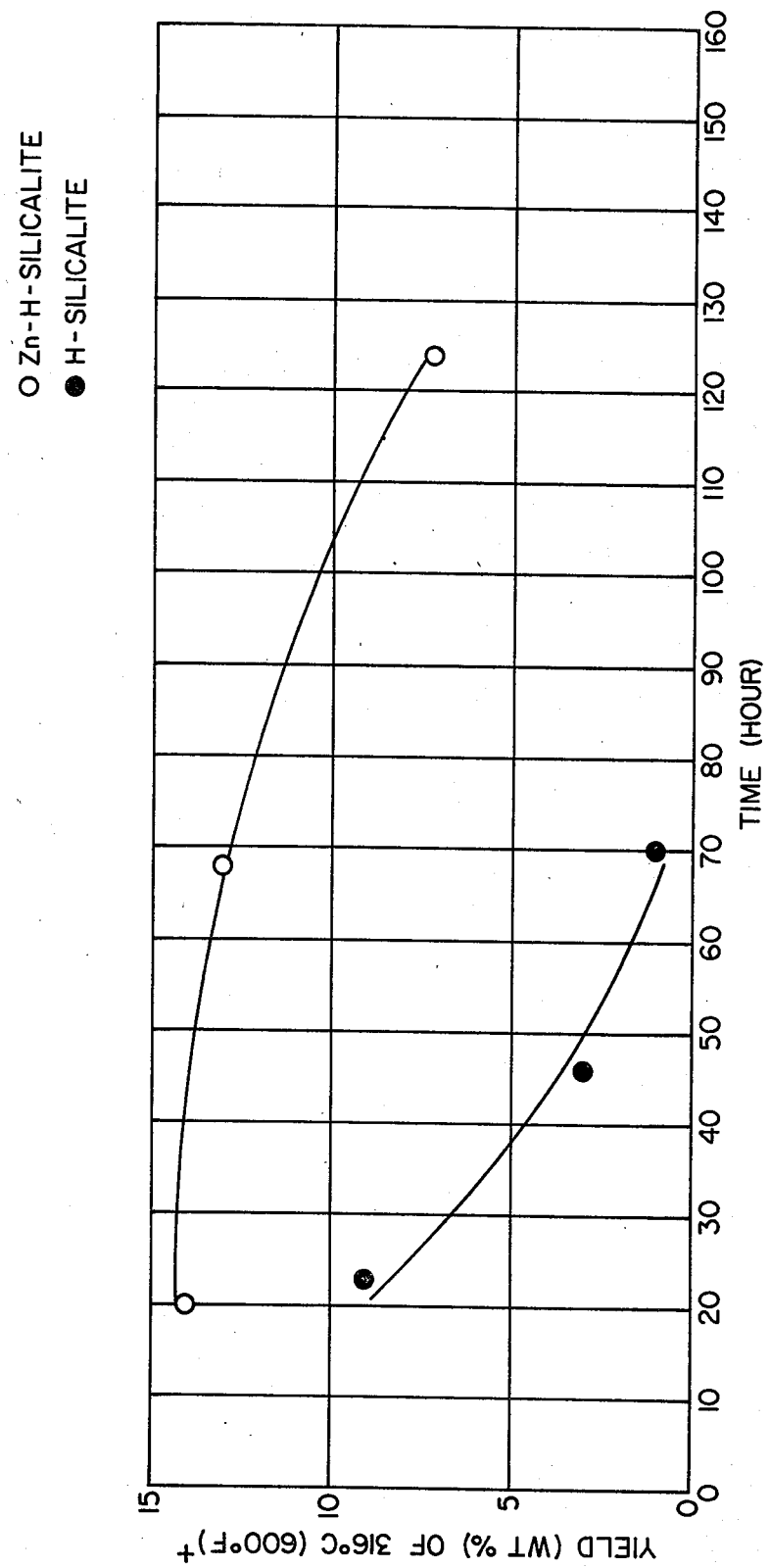

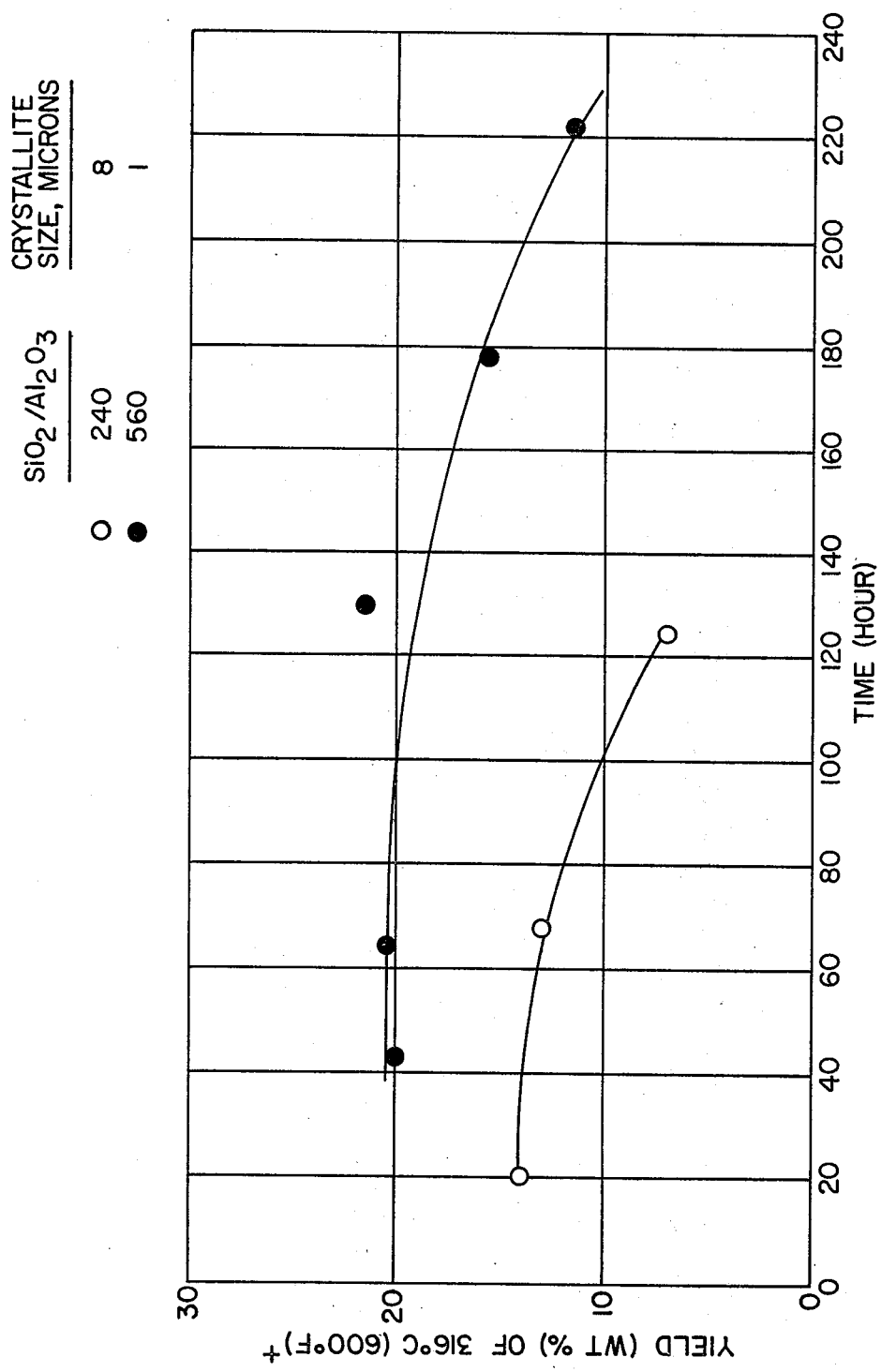

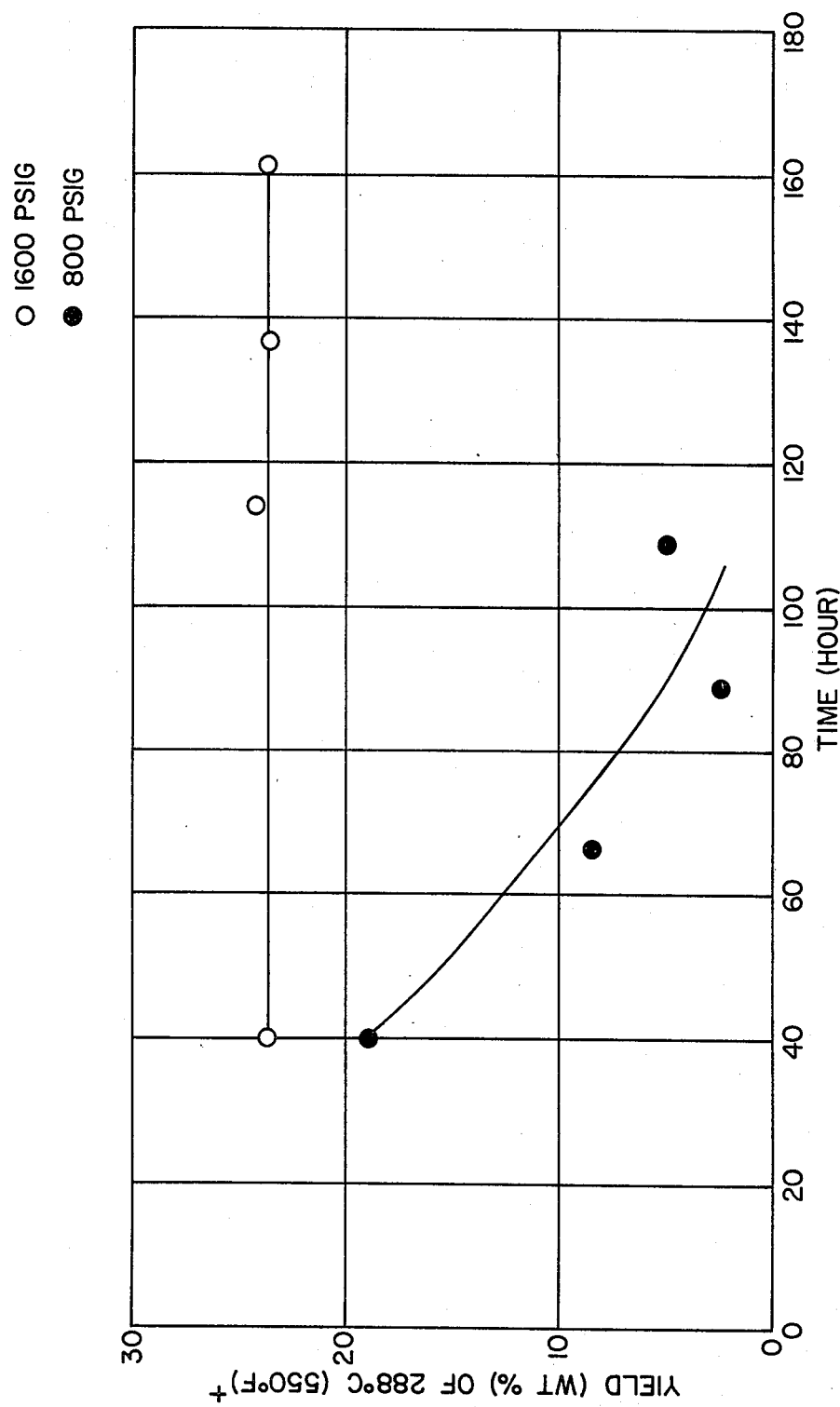
FIG._4.

OLIGOMERIZATION OF GASEOUS OLEFINS

TECHNICAL FIELD

Medium and heavy olefins are chemicals which are highly useful and desirable compounds. These compounds can be used without further reaction as components of functional fluids as lubricants, as viscosity index improvers to lubricants, as hydraulic fluids, as transmission fluids, and as insulating oils, e.g., in transformers to replace PCB containing oils. These olefins can also undergo chemical reactions to produce surfactants which in turn can be used as additives to improve the operating characteristics of the compositions to which they are added (e.g., lubricating oils), or can be used as primary surfactants in highly important activities such as enhanced oil recovery or as detergents. Among the most used surfactants prepared from heavy olefins are alkyl sulfonates and alkyl aryl sulfonates.

Light alkenes, especially propenes and butenes, are light gas products from a large number of synthetic processes. They are produced as offgases in catalytic cracking and as products of synthetic fuel preparation techniques.

It can be appreciated that there is a continuing search for more efficient methods for using light olefins and for preparing the heavier, more valuable olefins.

The typical methods of preparing heavier olefins use 1-alkenes (alpha-olefins) as the reactants. In a typical process, 1-octene, 1-decene, 1-tetradecene or mixtures thereof are oligomerized and heavy olefin mixtures comprising trimers, tetramers and pentamers of the reactants are recovered. The processes are typically catalytic and typically use multiphase systems. Other oligomerization types of processes use phosphoric acid containing catalysts to prepare gasoline range materials. Three major modifications involving phosphoric acid catalysts include (1) quartz wetted with liquid phosphoric acid, (2) phosphoric acid impregnated pellets (e.g., kieselguhr) used in reaction chambers, and (3) phosphoric acid impregnated catalyst pellets packed in tubes surrounded by cooling water. Additionally, copper pyrophosphate has been used as a catalyst.

More recent processes for producing heavy olefins for synthetic lubricants, as opposed to gasoline range fuels, use boron trifluoride as the catalyst, together with promoters (e.g., $BF_3$-decanol or $BF_3$-acetic acid complexes), or with cocatalysts. Reaction conditions typically include temperatures of less than 100° C. and pressures of less than 7 bar. The reactions are carried out in solutions which contain the $C_8$ or greater alkene reactants and the $BF_3$-complex or the cocatalyst. Gaseous $BF_3$ is typically added by bubbling through the solution. Cocatalysts include many organic compounds, such as esters, polyols, aliphatic alcohols, aliphatic ethers, aliphatic carboxylic acids, ketones, aldehydes and acid anhydrides.

A number of patents have issued relating to the preparation of substituted benzene aromatics from short chain olefins using highly active zeolites such as ZSM-5 (e.g., U.S. Pat. No. 3,756,942, Cattanach, Sept. 4, 1973; U.S. Pat. No. 3,827,968, Givens et al., Aug. 6, 1974; U.S. Pat. No. 3,960,978, Givens et al., June 1, 1976). Additionally, several patents disclose the preparation of gasoline and fuel oil range materials from short chain olefins such as propene and ethene (e.g., U.S. Pat. No. 4,227,992, Garwood et al., Oct. 14, 1980; U.S. Pat. No. 4,211,640, Garwood et al., July 8, 1980).

Even with the existence of phosphoric acid and zeolitic processes for making gasoline and of boron trifluoride processes for making heavy olefins, it can be appreciated that there is a continuing search for efficient methods of heavy olefin preparation which use available materials, do not require solvent recovery steps or use of liquid solutions, and yet which are efficient.

I have discovered that under certain reaction conditions, the shorter chain alkenes can be polymerized over intermediate pore size crystalline molecular sieves to highly desirable, heavier, longer chain alkenes. Surprisingly, intermediate pore size molecular sieves can catalyze these reactions even though they would have been expected to aromatize the feed alkenes or product oligomers or to crack the product alkene oligomers.

By using a combination of conditions which maintain the light alkene reactant as a gas but which require the liquefaction of higher molecular weight alkene polymers, surprisingly long run lives can be obtained. Further, extremely high quality midbarrel fuels, such as jet fuel can be produced, in addition to still higher molecular weight products which are highly useful intermediates in preparing surfactants. Further, by using my discoveries, the effective capacity of reactors such as catalytic crackers can be increased since the volume of gas produced can be easily and efficiently reduced. The combination of high pressures and low temperatures favors oligomerizing a gaseous olefin reactant rather than cracking or reactions such as cyclizing which lead to hydrogen transfer reactions of reactant and product. High pressure and low temperature also favor forming higher molecular weight alkene liquids.

TECHNICAL DISCLOSURE

My discoveries are embodied in a process for oligomerizing alkenes, comprising:
(a) contacting under oligomerization conditions a feed comprising one alkene which is a gas under said oligomerization conditions with a catalyst comprising an intermediate pore size silicaceous crystalline molecular sieve substantially free of hydrogen transfer activity; and
(b) recovering an effluent comprising oligomerized alkenes wherein at least some of said oligomerized alkenes are liquid under said oligomerization conditions.

My discoveries are also embodied in a process for oligomerizing alkenes, comprising:
(a) contacting under oligomerization conditions a feed comprising a mixture of alkenes wherein at least some of the alkenes in said alkene mixture are gases under said oligomerization conditions with a catalyst comprising an intermediate pore size silicaceous crystalline molecular sieve substantially free of hydrogen transfer activity; and
(b) recovering an effluent comprising alkene oligomers of said liquid alkenes wherein at least some of said alkene oligomers are liquids under said oligomerization conditions.

My discoveries are further embodied in a process for oligomerizing alkenes, comprising:
(a) contacting under oligomerization conditions a feed consisting of an alkene mixture wherein at least some of the alkenes in said feed are gases under said oligomerization conditions with a catalyst comprising an intermediate pore size silicaceous crystalline molecular sieve substantially free of hydrogen transfer activity; and (b) recovering an effluent comprising alkene oligomers of said liquid alkenes wherein at least some of said alkene oligomers are liquids under said oligomerization conditions.

The feeds used in the present process contain alkenes which are gases under the conditions in the oligomerization reaction zone. Under standard operating procedures, it is normal both to know the chemical composition of feedstocks being introduced into a reaction zone and to set and control the temperature and pressure in the reaction zone. Once the chemical composition of a feedstock is known, the temperatures and hydrocarbon partial pressures which will maintain all or part of the feed alkenes as gases can be determined using standard tables or routine calculations. Conversely, once the desired temperature and pressure to be used in the reaction zone are set, it becomes a matter of routine to determine what feeds and feed components would or would not be gases in the reactor. These calculations involve using critical temperatures and pressures. Critical temperatures and pressures for pure organic compounds can be found in standard reference works such as *CRC Handbook of Chemistry and Physics, International Critical Tables, Handbook of Tables for Applied Engineering Science,* and Kudchaker, Alani, and Zwolinski, Chemical Reviews, 68, 659 (1968), all of which are incorporated herein by reference. The critical temperature for a pure compound is that temperature above which the compound cannot be liquefied regardless of pressure. The critical pressure is the vapor pressure of the compound at its critical temperature. These points for several pure alkenes are listed below:

|  | $T_c$ °C. (°F.) | $P_c$-atm(bar) |
|---|---|---|
| ethene | 9.21 (48.6) | 49.66 (50.3) |
| propene | 91.8 (197.2) | 45.6 (46.2) |
| 1-butene | 146.4 (295.5) | 39.7 (40.2) |
| 1-pentene | 191.59 (376.9) | 40 (40.5) |
| iso-2-pentene | 203 (397) | 36 (36.5) |
| 1-hexene | 230.83 (447.49) | 30.8 (31.2) |
| 1-heptene | 264.08 (507.34) | 27.8 (28.2) |
| 1-octene | 293.4 (560.1) | 25.6 (25.9) |

It can be appreciated that at temperatures above about 235° C. (455° F.), pure $C_6$ and lower alkenes must be gaseous, while pure $C_7$ and higher alkenes can still be liquefied by applying pressure. Similarly, above about 150° C. (302° F.) pure $C_5$ and higher alkenes can be maintained in the liquid state, while pure $C_4$ and lower alkenes must be gaseous.

Typical feeds are mixtures of compounds. But even so, once the chemical composition of the feed is known, the critical temperature and pressure of the mixture can be determined from the ratios of the chemicals and the critical points of the pure compounds. See for example, the methods of Kay and Edmister in *Perry's Chemical Engineers Handbook,* 4th Edition, pages 3-214, 3-215 (McGraw Hill, 1963), which is incorporated by reference.

Of course, the only constraint on the alkenes in the feed of the oligomerization reaction zone is that at least some of the alkenes be gases under the conditions in that zone (the conditions include a temperature of less than about 350°-400° C.). The chemical composition of the alkenes can be varied to obtain any desired reaction mixture or product mix, so long as some feed alkene components are gases.

The alkene chains can be branched. And, even though intermediate pore size molecular sieves are used as catalysts, alkenes such as 3,3-dimethyl-1-butene which has quaternary carbons (two branches on the same carbon atom) can be used. But where quaternary carbons are present, it is highly preferred that the branches are methyl. It appears that even though intermediate pore size molecular sieves do not admit quaternary carbon atoms into their pore structures, they have the capability of causing one of the quaternary substituents to migrate to a different position on the alkene chain, thereby forming two tertiary sites and an entity which can enter the intermediate sized pores.

The preferred alkenes are straight chain, or n-alkenes, and the preferred n-alkenes are 1-alkenes. The alkenes preferably have 2 to 6 carbon atoms. The most preferred alkenes are the compounds propene, 1-butene, 2-butene and 2-methylpropene as well as mixtures of them.

One of the surprising discoveries which my invention embodies is that under certain conditions, shorter chain alkenes can be oligomerized over the low hydrogen transfer activity intermediate pore size molecular sieves to very long chain compounds; and, extremely long run lengths are achieved under the high pressures.

The feed alkenes can be prepared from any source by standard methods. Sources of such feed alkenes can include FCC offgas, coker offgas, thermal cracking offgas, syngas (by use of CO reduction catalysts), low pressure, nonhydrogenative zeolitic dewaxing, alkanols (using high silica zeolites), and dewaxing with crystalline silica polymorphs. The alkenes can be in hydrocarbon streams with other hydrocarbonaceous compounds, but preferably, the feed is primarily alkenes.

By "intermediate pore size silicaceous crystalline molecular sieve," as used herein, is meant two classes of silica containing crystalline materials. The first class includes materials which, in addition to silica, contain significant amounts of alumina. These crystalline materials are usually called "zeolites," i.e., crystalline aluminosilicates. The second class of materials are essentially alumina free silicates. These crystalline materials can include crystalline silica polymorphs, e.g., silicalite, chromia silicates, e.g., CZM, and ferrosilicates, e.g. U.S. Pat. No. 4,238,318.

All of these materials have the ability of sorting molecules based on the size or the shape, or both of the molecules. The larger pore size materials will admit larger molecules than the smaller pore size materials. Intermediate pore size silicaceous crystalline molecular sieves have the unique characteristics of being able to differentiate between large molecules and molecules containing quaternary carbon atoms on the one hand, and smaller molecules on the other. Thus, the intermediate pore size materials have surprising catalytic selectivities by reason of their effective pore apertures, as well as highly desirable and surprising catalytic activity and stability when compared to the larger pore size crystalline molecular sieves.

By "intermediate pore size," as used herein, is meant an effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as the faujasites and mordenites, they can differentiate between n-alkanes and slightly branched alkanes on the one hand and larger branched alkanes having, for example, quaternary carbon atoms.

The effective pore size of the molecular sieves can be measured using standard adsorption techniques and hydrocarbonaceous compounds of known minimum kinetic diameters. See Breck, *Zeolite Molecular Sieves*, 1974 (especially Chapter 8) and Anderson et al, J. Catalysis 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. Among the materials falling within this range are the zeolite ZSM-5, the crystalline silica polymorph silicalite, RE 29,948 organosilicates, and the chromia silicate, CZM.

In performing adsorption measurements to determine pore size, standard techniques are used. It is convenient to consider a particular molecule as excluded if it does not reach at least 95% of its equilibrium adsorption value on the zeolite in less than about 10 minutes (p/po=0.5; 25° C.).

Examples of intermediate pore size silicaceous crystalline molecular sieves include zeolites such as CZH-5 and members of the ZSM series, e.g., ZSM-5, ZSM-11, ZSM-12, ZSM-21, ZSM-23, ZSM-35, and ZSM-38. ZSM-5 is described in U.S. Pat. Nos. 3,702,886 and 3,770,614; ZSM-11 is described in U.S. Pat. No. 3,709,979; ZSM-12 is described in U.S. Pat. No. 3,832,449; ZSM-21 and ZSM-38 are described in U.S. Pat. No. 3,948,758; ZSM-23 is described in U.S. Pat. No. 4,076,842; ZSM-35 is described in U.S. Pat. No. 4,016,245; CZH-5 is disclosed in Ser. No. 166,863, Hickson, filed July 7, 1980. These patents and specifications are incorporated herein by reference. The intermediate pore size materials can include "crystalline admixtures" which are thought to be the result of faults occurring within the crystal or crystallite area during the synthesis of the zeolites. The "crystalline admixtures" are themselves zeolites but have characterisics in common, in a uniform or nonuniform manner, to what the literature reports as distinct zeolites. Examples of crystalline admixtures of ZSM-5 and ZSM-11 are disclosed and claimed in U.S. Pat. No. 4,229,424, Kokotailo, Oct. 21, 1980 (incorporated by reference). The crystalline admixtures are themselves intermediate pore size zeolites and are not to be confused with physical admixtures of zeolites in which distinct crystals or crystallites of different zeolites are physically present in the same catalyst composite or hydrothermal reaction mixture.

Other examples of intermediate pore size silicaceous crystalline molecular sieves include crystalline silica polymorphs which, as described before, are essentially alumina free.

"Essentially alumina free," as used herein, is meant the product silica polymorph (or essentially alumina-free silicaceous crystalline molecular sieve) has a silica:alumina mole ratio of greater than 200:1, preferably greater than 500:1, and more preferably greater than 1000:1. The term "essentially alumina free" is used because it is difficult to prepare completely aluminum free reaction mixtures for synthesizing these materials. Especially when commercial silica sources are used, aluminum is almost always present to a greater or lesser degree. The hydrothermal reaction mixtures from which the essentially alumina free crystalline silicaceous molecular sieves are prepared can also be referred to as being substantially aluminum free. By this usage is meant that no aluminum is intentionally added to the reaction mixture, e.g., as an alumina or aluminate reagent, and that to the extent aluminum is present, it occurs only as a contaminant in the reagents.

Intermediate pore size crystalline silicas include silicalite, as disclosed in U.S. Pat. No. 4,061,724; "RE 29,948 organosilicates" as disclosed in RE 29,948; and CZH-9, Ser. No. 264,767, Hickson, filed May 18, 1981. Intermediate pore size silicas, ferrosilicates and galliosilicates are disclosed in U.S. Pat. No. 4,238,318, Kouwenhoven et al, Dec. 9, 1980. Intermediate pore size chromia silicates, CZM, are disclosed in Ser. No. 160,618, Miller, filed June 28, 1980. All of these are incorporated by reference herein.

The most preferred molecular sieves are the zeolites ZSM-5, ZSM-11, and their crystalline admixtures, silicalite, RE 29,948 organosilicates, and the chromia silicate CZM. Of course, these and other molecular sieves can be used in physical admixtures.

The silicaceous crystalline molecular sieves must be substantially free of hydrogen transfer activity. High hydrogen transfer activity is typically present in a catalyst as a result of a high aluminum content (low silica:alumina mole ratio) in a molecular sieve component. If the silica:alumina ratio is low, the catalyst will tend to convert the olefinic products and reactants to paraffins and aromatics rather than to oligomerize them, thereby greatly reducing or eliminating the benefits of the present invention. (Hydrogen transfer activity is to be distinguished from hydrogenation activity, which would saturate the alkenes to produce the corresponding alkanes.) The hydrogen transfer activity of the molecular sieve can be substantially lessened by using essentially alumina free silicaceous crystalline molecular sieves, and especially materials such as silicalite, RE 29,948 organosilicates, and CZM.

Zeolitic silicaceous crystalline molecular sieve catalysts can be made substantially more active and stable for oligomerization by including the Group IIB metals, zinc or cadmium. A primary characteristic of these substituents is that they are weak bases, and are not easily reduced. These metals can be incorporated into the catalysts using standard impregnation, ion exchange, etc., techniques. Other metals such as calcium and the rare earths may be included in the catalyst. If hydrogen is not added to the feed, Group VIII metals (such as nickel, cobalt, palladium, and platinum) as well as other metals (such as chromium, vanadium, titanium, manganese, and rhenium) may be included in the catalyst. Mixtures of these metals may also be present. Strongly basic metals such as the alkali metals are unsatisfactory as they poison substantially all of the polymerization sites on the zeolite. For this reason, the alkali metal content of the zeolite is less than 1%, preferably less than 0.1%, and most preferably less than 0.01%. The most preferred substituents for use are zinc and cadmium, of these zinc is preferred. The amount of zinc or cadmium used is typically from about 0.01 to about 10 wt. %.

The use of zinc or zinc compounds as the substituent on the zeolitic molecular sieves, and even on the essentially alumina free materials, gives surprising stability, yields, and activity in the gaseous olefin oligomerization processes described herein.

The substantial absence of hydrogen transfer activity can be determined using standard laboratory procedures.

The polymerization processes of the present invention are surprisingly more efficient with small crystallite sieve particles than with larger crystalline particles. Preferably, the molecular sieve crystals or crystallites are less than about 40 microns, more preferably less than about 1 micron, and most preferably less than about 0.1 micron in the largest dimension. Methods for making molecular sieve crystals in different physical size ranges are known to the art.

The molecular sieves can be composited with inorganic matrix materials, or they can be used with organic binders. It is preferred to use an inorganic matrix, since the molecular sieves, because of their large internal pore volumes, tend to be fragile, and to be subject to physical collapse and attrition during normal loading and unloading of the reaction zones as well as during the oligomerization processes. Where an inorganic matrix is used, it is highly preferred that the matrix be substantially free of hydrocarbon conversion activity. It can be appreciated that if an inorganic matrix having hydrogen transfer activity is used, a significant portion of the oligomers which are produced by the molecular sieve may be converted to paraffins and aromatics and to a large degree the benefits of my invention will be lost.

The reaction conditions under which the oligomerization reactions take place include hydrocarbon partial pressures sufficient to maintain the desired alkene reactants in the gaseous state in the reaction zone, while causing at least some of the oligomer products to be liquids. Of course, the smaller the alkene molecules, the lower the minimum temperature required to maintain the gaseous state. As described above, the pressure and temperature are intimately related to the chemical composition of the feed, but can be readily determined. Thus, the required temperatures can range from above 231° C. for a pure n-1-hexene feed to above 147° F. for a pure butene feed.

The reaction zone is typically operated below about 350° C. Above that temperature not only significant cracking and loss of oligomer product take place, but also significant hydrogen transfer reactions causing loss of olefinic oligomers to paraffins and aromatics. Reaction zone temperatures are typically above 50° C. Pressures are above about 30 bar to maintain liquid product, and are preferably above about 65 bar. Liquid hourly space velocities can range from 0.05 to 20, preferably from 0.1 to about 4.

Once the effluent from the oligomerization reaction zone is recovered, a number of further processing steps can be performed.

The alkene oligomers produced are particularly suitable for use in the synthesis of detergents, especially to produce alkylbenzene sulfonate surfactants.

All or part of the effluent can be contacted with the molecular sieve catalyst in further reaction zones to furth react unreacted alkenes and alkene oligomers with themselves and each other to form still longer chain materials. Of course, the longer the carbon chain, the more susceptible the compound is to being cracked. Therefore, where successive oligomerization zones are used, the conditions in each zone must not be so severe as to crack the oligomers. Preferably, the reaction conditions in each of the succeeding zones are less severe than in the oligomerization zone which immediately precedes it. operating with oligomerization zones in series with decreasing severity can also make process control of the exothermic oligomerization reactions much easier.

One particularly desirable method of operation is to separate unreacted alkenes present in the effluent from the alkene oligomers present in the effluent and then to recycle the unreacted alkenes back into the feed.

The run life of the catalyst in the oligomerization reaction zone can be greatly and surprisingly increased by periodically stopping the flow of feed into the reaction zone and stripping the catalyst with a stripping gas (such as hydrogen, nitrogen, or water vapor).

FIGURES

FIG. 1 illustrates data showing differences between the hydrogen transfer indices of several catalysts as well as the response of the hydrogen transfer indices to fouling.

FIG. 2 shows data illustrating the greater stability of a Zn-silicalite catalyst over an H-silicalite catalyst.

FIG. 3 shows data illustrating the effect of crystallite size on high pressure oligomerization.

FIG. 4 shows data illustrating the effect of pressure on fouling characteristics and 288° C.+ product from 1-butene.

EXAMPLE 1

A series of experiments was performed to examine the hydrogen transfer activity of molecular sieves. A feed pulse of fixed volume (0.5 microliter) from a heated Valco valve was carried into a small, fixed catalyst bed located in a stainless steel reactor. The reaction was entirely gas phase and isothermal. The hydrocarbon feed pulse was carried to the catalyst bed by a known velocity nitrogen stream at a high linear rate. The nitrogen stream was passed through a 4A/5A molecular sieve purifier before contacting the feed. The catalyst bed contained −250 mesh catalyst fines which, depending on the catalyst, were diluted with the same size mesh alumina. The diluent alumina was added as needed to reduce the catalyst activity so all catalysts could be measured at roughly identical feed conversions. The catalyst was finally diluted (4:1) with 80–100 mesh, acid washed Alundum to improve catalyst dispersion and to help maintain a true isothermal bed temperature. Reactor pressure was controlled by an Annin valve.

The entire gas stream, containing the reacted feed pulse, was taken directly through heated lines to the injector splitter of a capillary gas chromatograph equipped with a flame ionization detector.

The reaction conditions include a catalyst temperature of 221° C. (430° F.), total pressure of 34.5 bar (500 psi) and a nitrogen carrier gas flow of 800 cc/min. at STP. The injection volume was 0.5 microliter. Hydrocarbon analysis was performed using a 50-meter OV-101 fused silica capillary column. The catalyst was continually exposed to the nitrogen carrier gas between injections.

The hydrogen transfer index calculated from the test results is the ratio of 3-methylpentenes to 3-methylpentane produced from a 1-hexene feed, with a linear hexene conversion from 30% to 70%.

The contact time was computed from the temperatures and pressure corrected linear velocity of the nitrogen carrier stream and the length and volume of the catalyst bed. The computed WHSV and catalyst/oil ratio were based solely on the active component content within the bed.

The catalysts tested are listed in Table 1.

TABLE 1

| | Catalyst | $SiO_2/Al_2O_3$ Mole Ratio |
|---|---|---|
| (A) | ZSM-5 | 78:1 |
| (B) | Silicalite | 230:1 |
| (C) | Silicalite | 2200:1 |
| (D) | Ultrastable Y | 6:1 |
| (E) | Dealuminated Mordenite | 63:1 |
| (F) | Amorphous $SiO_2/Al_2O_3$ | 54/46 (wt. ratio) |
| (G) | CZH-5 | 50:1 |

The results obtained are listed in Table 2. Experiments with Catalysts (A) and (B) were performed after impregnating the catalysts with 0.8 weight percent zinc.

EXAMPLE 2

An experiment was performed to investigate the reaction of an alkene having a quaternary carbon over an intermediate pore size zeolite. The feed was 3,3-dimethyl-1-butene.

| | Run A | Run B |
|---|---|---|
| Temperature °C. (°F.) | 204 (400) | 204 (400) |
| Hydrocarbon Pressure | atm | 551 (800 psig) |
| LHSV | 0.33 | 0.33 |
| Catalyst | Zn-ZSM-5 (1% Zn) 65% ZSM-5/ 35% $Al_2O_3$ | Zn-ZSM-5 (1% Zn) 65% ZSM-5/ 35% $Al_2O_3$ |
| Feed Conversion to $C_7+$ | 1% | 55% |

Of the $C_7+$ compounds produced in Run B, about 50% were $C_{12}$ hydrocarbons. The data show that a highly unusual reaction has taken place.

EXAMPLE 3

An experiment was performed to compare CZM to silicalite impregnated with chromium for oligomerizing 1-butene at 110 bar (1600 psig) hydrocarbon pressure, 288° C. (550° F.) and LHSV 1.5.

| | Cr (Wt. %) | Al (ppm) | Na (ppm) |
|---|---|---|---|
| Cr-Silicalite | 0.5 | 400 | 100 |
| CZM | 0.46 | 570 | 140 |

The following data show that CZM is more active than the impregnated material.

TABLE 2

| Catalyst | 20% A 80% $Al_2O_3$ | 20% A 80% $Al_2O_3$ | 65% B | 65% C | 12% D 88% $Al_2O_3$ | 18% E 82% $Al_2O_3$ | 100% F | 100% G |
|---|---|---|---|---|---|---|---|---|
| Inj. Number | 3 | 3 | 3 | 2 | 3 | 1 | 2 | 1 |
| Catalyst Wt (mg Sieve) | 4.4 | 4.1 | 19 | 24 | 2.8 | 4.2 | 35 | 19.3 |
| Zn (0.8%): Yes/No | No | Yes | Yes | No | No | No | No | No |
| Alundum Dilution | 4:1 | 4:1 | 4:1 | 3:1 | 4:1 | 4:1 | 4:1 | 4:1 |
| Contact Time (sec) | 0.25 | 0.36 | 0.33 | 0.41 | 0.28 | 0.23 | 0.34 | 0.4 |
| WHSV (1/hr) | 1100 | 806 | 200 | 120 | 1500 | 1220 | 100 | 157 |
| Cat/Oil | 13 | 12 | 57 | 71 | 9 | 13 | 104 | 57 |
| Conversion From Linear Hexenes (%) | 47 | 42 | 41 | 56 | 38 | 48 | 43 | 53 |
| $K_{Hexenes}$ (1/sec) | 2.54 | 1.51 | 1.60 | 2.00 | 1.71 | 2.84 | 1.65 | 1.88 |
| Product Yield, Wt % | | | | | | | | |
| $C_4$ Minus | 13 | 12.6 | 14 | 13.3 | 3.5 | 17.1 | 0.3 | 12 |
| $C_5$ | 11 | 10 | 8.4 | 8.5 | 4.2 | 12.9 | 3 | 8 |
| $C_6$ | 57 | 58.8 | 62 | 53.6 | 63.2 | 55.7 | 76.4 | 73 |
| $C_7$ | 4 | 4.2 | 4.1 | 5.5 | 4.7 | 4.4 | 3.5 | 2 |
| $C_8$ | 7.5 | 5.6 | 5.4 | 7.9 | 5.9 | 5.2 | 4.1 | 3.7 |
| $C_9$ | 4 | 3.6 | 2.5 | 4.3 | 4.3 | 2.4 | 2.4 | 1.3 |
| $C_{10}+$ | 1.9 | 2.8 | 2.3 | 4.9 | 10.7 | 1.1 | 10.1 | 0.3 |
| Hydrogen Transfer Index | | | | | | | | |
| 3M-Pentenes/ 3M-Pentane | 66 | 70 | 105 | 500 | 0.30 | 1.0 | 5 | 6 |

The graph of FIG. 1 illustrates the differences in hydrogen transfer index for several catalysts, as well as the response of the hydrogen transfer index to the number of hexene injections, i.e., to the fouling of the catalyst. The higher the hydrogen transfer index, the lower the hydrogen transfer activity of the catalyst. The hydrogen transfer index should be above 10, preferably above 25.

| | Time (Hr.) | 350° F. + Wt. % of Product |
|---|---|---|
| Cr-Silicalite | 17 | 5 |
| CZM | 46 | 43 |

The test using CZM was continued to 80 hours, the time at which the CZM activity fell to the level of the impregnated silicalite at 17 hours.

EXAMPLE 4

Propene was oligomerized over three catalysts, each containing 1% zinc. The reaction conditions and results appear in Table 3.

TABLE 3

| Catalyst | Zn-HZSM-5 | Zn-HZSM-5 | Zn-H—Silicalite |
|---|---|---|---|
| Hydrocarbon Pressure bar (psig) | 27.6 (400) | 110 (1600) | 110 (1600) |
| LHSV | 2 | 0.5 | 0.5 |
| Temperature °C. (°F.) | 288 (550) | 288 (550) | 288 (550) |
| Product Yields, Wt. % | | | |
| $C_3-C_4$ | 9.2 | 11.1 | 6.8 |
| $C_5$-177° C. (350° F.) | 30.3 | 26.9 | 37.3 |
| 177° C.+ | 60.5 | 62.0 | 55.9 |
| 371° C.+ | 3.2 | 12.5 | 4.3 |
| F-1/F-2, 93–177° C. | 95/80 | 74/72 | 87/78 |
| Olefins, 177° C.+, % | — | 15 | 50 |
| Hydrofined 177–288° C. | | | |
| Freeze Pt, °C. (°F.) | −70 (−94) | <−70 (−94) | <−70 (−94) |
| Smoke Pt, mm | 35 | <20 | 28 |

The olefinicity of the Zn-HZSM-5 93°–177° C. (200°–350° F.) product produced at 27.6 bar was high as reflected by the high octane. Increasing the pressure increased the 371° C. (700° F.)+ fraction but decreased olefinicity. Using a silicalite based catalyst instead of a ZSM-5 based catalyst increased the olefin content of the product.

EXAMPLE 5

An experiment was performed to examine the effect of zinc on high pressure oligomerization with intermediate pore size molecular sieves. A silicalite and zinc impregnated silicalite were used as catalysts. The propene feed was contacted with the catalyst at LHSV of 1, hydrocarbon pressure of 110 bar (1600 psig) and 288° C. (550° F.). The data are shown in FIG. 2. At 20 hours onstream, the yield of 316° C. (600° F.)+ fraction was 9 wt. % for the silicalite catalyst but 14 wt. % for the zinc-silicalite catalyst. At 50 hours onstream, the silicalite catalyst produced only 2% 316° C.+ while the zinc-containing catalyst took 150 hours to reach that point.

EXAMPLE 6

Propene was oligomerized over a zinc (1 wt. %) containing ZSM-5 catalyst at 27.6 bar (400 psig), 288° C. (550° F.) and LHSV of 4. The results appear in Table 4.

TABLE 4

| Product Yields, Wt. % | |
|---|---|
| $C_1-C_2$ | 0 |
| $C_3$ | 3.5 |
| $C_4$ | 5.7 |
| $C_5$-93° C. (200° F.) | 6.6 |
| 93–177° C. (200–350° F.) | 23.7 |
| 177° C. (350° F.)+ | 60.5 |
| 93–177° C. Product | |
| P/N + O/A | 8.7/90.8/0.5 |
| Gum, mg/100 ml | 1.0 |
| Maleic Diene Value | 0 |
| F-1/F-2 | 95/80 |
| 177° C.+ Product | |
| P/N + O/A | 17.0/79.2/3.8 |

The 177° C.+ fraction of the product was hydrofined at 329° C. (625° F.) and 34.5 bar (500 psig) over a Ni-Mo/Al₂O₃ catalyst. The product characteristics are compared to ASTM specifications for Jet A-1 and No. 2 Diesel in Table 5.

TABLE 5

| | | ASTM Specs |
|---|---|---|
| 177–288° C. (350–550° F.) Product (75 Wt. %) | | Jet A-1 |
| Gravity, °API | 52.9 | 37–51 |
| Bromine No. | 1.6 | |
| P/N/A | 83.7/13.8/2.5 | A < 20 |
| P/N/A, ndM | 87.3/12.7/0.05 | |
| Viscosity, | | |
| −20° C. (−4° F.), cs | 6.6 | <8 |
| 38° C. (100° F.), cs | 1.6 | |
| Freeze Pt | <−70° C. (−94° F.) | <−50° C. (−58) |
| Smoke Pt, mm | 35 | >25 |
| | | No. 2 |
| 288° C.+ Product (25 Wt. %) | | Diesel |
| P/N/A | 65.5/28.2/6.3 | |
| P/N/A, ndM | 83.1/15.5/1.4 | |
| Viscosity, 40° C., cs | 6.8 | 1.9–4.1 |
| Pour Pt/Cloud Pt, °C. (°F.) | −59/−29 (−75/−20) | |
| Calc. Cetane Index | 75 | >40 |
| Distillation, Simulated TBP, °C. | | |
| 10/30 | 280/301 | |
| 50/70 | 321/342 | |
| 90/EP | 387/462 | |

EXAMPLE 7

An experiment was performed which shows the benefits of controlling the size of the molecular sieve crystallite. Propene was oligomerized over 1 wt. % zinc-containing silicalite catalysts at 110 bar (1600 psig), 288° C. (550° F.), and LHSV of 0.5. The activity of the catalysts for producing high molecular weight oligomers, 315° C. (600° F.)+ fraction, is shown in FIG. 3.

EXAMPLE 8

An experiment was performed to compare the effect of pressure on run length and liquid yield using a zinc (1 wt. %) containing silicalite catalyst and a 1-butene feed. The reaction conditions included 288° C. (550° F.), LHSV of 0.5, and a pressure of either 55.1 bar (800 psig) or 110.2 bar (1600 psig). The wt. % of liquid product boiling above 288° C. (550° F.) as a function of time onstream is shown in FIG. 4.

From the true boiling point distillation of the product at 55 bar at 42 hours and at 89 hours, the percent of the product which was liquid phase was calculated using standard methods and critical temperatures and pressures. The true boiling point data, corrected for gas in the reactor effluent, were as follows:

| LV % | 42 Hours °C. (°F.) | 89 Hours °C. (°F.) |
|---|---|---|
| Start | −8 (18) | −10 (14) |
| 5/10 | −8/67 (18/152) | −10/−10 (14/14) |
| 20/30 | 118/143 (245/290) | 7/12 (45/53) |
| 50 | 201 (393) | 110 (231) |
| 70/80 | 248/276 (478/529) | 124/153 (256/308) |
| 90/95 | 323/359 (613/678) | 198/254 (389/489) |
| 99/End Point | 431/504 (807/940) | 337/454 (638/850) |

The calculated fraction of the product which was in the liquid phase was:

| Hours | % in Liquid Phase | 288° C.+ Fraction (Wt. %) |
|---|---|---|
| 42 | 100 | 19 |
| 89 | 7 | 2 |

These data show the benefit of operating at very high pressures, 110 bar as opposed to 55 bar. They also show that as the catalyst ages, it gradually loses the ability to oligomerize reactants to products which are liquid.

What is claimed is:

1. A process for oligomerizing alkenes, comprising:
   (a) contacting under oligomerization conditions a feed comprising one alkene which is a gas under said oligomerization conditions with a catalyst comprising an intermediate pore size silicaceous crystalline molecular sieve substantially free of hydrogen transfer activity selected from silicalite, an organosilicate disclosed in RE 29,948, CZM or mixtures thereof; and
   (b) recovering an effluent comprising oligomerized alkene wherein at least some of said oligomerized alkenes are liquid under said oligomerization conditions.

2. A process for oligomerizing alkenes, comprising:
   (a) contacting under oligomerization conditions a feed comprising a mixture of alkenes wherein at least some of the alkenes in said alkene mixture are gases under said oligomerization conditions with a catalyst comprising an intermediate pore size silicaceous crystalline molecular sieve substantially free of hydrogen transfer activity selected from silicalite, an organosilicate disclosed in RE 29,948, CZM or mixtures thereof; and
   (b) recovering an effluent comprising alkene oligomers of said gaseous alkenes wherein at least some of said alkene oligomers are liquids under said oligomerization conditions.

3. A process for oligomerizing alkenes, comprising:
   (a) contacting under oligomerization conditions a feed consisting of an alkene mixture wherein at least some of the alkenes in said feed are gases under said oligomerization conditions with a catalyst comprising an intermediate pore size silicaceous crystalline molecular sieve substantially free of hydrogen transfer activity selected from silicalite, an organosilicate disclosed in RE 29,948, CZM or mixtures thereof; and
   (b) recovering an effluent comprising alkene oligomers of said gaseous alkenes wherein at least some of said alkene oligomers are liquids under said oligomerization conditions.

4. The process of claim 2 or 3 in which substantially all of the alkenes in said alkene mixture are gases under said oligomerization conditions.

5. The process of claim 4 wherein said oligomerization conditions include a temperature higher than the critical temperature of the alkene having the highest critical temperature of the alkenes in said alkene mixture.

6. The process of claim 1, 2, or 3 in which said oligomerization conditions include a temperature of less than about 350° C.

7. The process of claim 6 wherein said oligomerization conditions include a pressure greater than about 30 bar and a temperature above about 100° C.

8. The process of claim 1, 2, or 3 wherein said alkenes comprise branched chain alkenes and wherein the branches of said branched chain alkenes are methyl branches.

9. The process of claim 8 wherein said alkenes have from about 2 to 6 carbon atoms.

10. The process of claim 1, 2, or 3 wherein said alkenes comprise n-alkenes.

11. The process of claim 10 wherein said n-alkenes are 1-alkenes.

12. The process of claim 10 wherein said alkenes have from about 2 to 6 carbon atoms.

13. The process of claim 1 wherein said alkene is selected from propene, 1-butene, 2-butene, and 2-methylpropene.

14. The process of claim 13 wherein said oligomerization conditions include a pressure greater than about 65 bar.

15. The process of claim 2 or 3 wherein said alkenes comprise propene, 1-butene, 2-butene, 2-methylpropene, and mixtures thereof.

16. The process of claim 15 wherein said oligomerization conditions include a pressure greater than about 65 bar.

17. The process of claim 1, 2, or 3 wherein said catalyst further comprises zinc or a compound thereof, nickel or a compound thereof, cadmium or a compound thereof, or mixtures thereof.

18. The process of claim 1, 2, or 3, further comprising the step of: hydrogenating said alkene oligomers.

19. The process of claim 1, 2, or 3, further comprising the steps of: periodically removing said catalyst from contact with said feed, stripping said catalyst with a stripping gas, and resuming said contacting under oligomerization conditions.

20. The process of claim 1, 2, or 3, further comprising the steps of: separating unreacted alkenes present in said effluent from alkene oligomers present in said effluent and recycling said unreacted alkenes into the feed for said contacting step.

21. The process of claim 1, 2, or 3, further comprising the step of: further contacting at least part of the unreacted alkenes and alkene oligomers present in said effluent with a catalyst comprising an intermediate pore size silicaceous crystalline molecular sieve substantially free of hydrogen transfer activity in at least one further reaction zone under further oligomerization conditions wherein said further oligomerization conditions are not so severe as to crack oligomers present in the effluent of said further reaction zone.

22. The process of claim 21 in which the further oligomerization conditions in said further reaction zone are less severe than the reaction conditions of the oligomerization reaction zone immediately preceding said further reaction zone.

* * * * *

UNITED STATES PATENT AND TRADEMARK OFFICE
CERTIFICATE OF CORRECTION

PATENT NO. : 4,423,269
DATED : December 27, 1983
INVENTOR(S) : STEPHEN J. MILLER It is certified that error appears in the above–identified patent and that said Letters Patent are hereby corrected as shown below:

Col. 3, line 37, "°C. (°F.)" should read --°C (°F)--.

Col. 3, line 64, "feed of the" should read --feed to the--.

Col. 4, line 23, "under certain conditions" should read --under certain reaction conditions--.

Col. 8, line 9, "furth" should read --further--.

Col. 8, line 18, "operating" should read --Operating--.

Col. 11, line 48, "contaning" should read --containing--.

Signed and Sealed this

Tenth Day of July 1984

[SEAL]

Attest:

GERALD J. MOSSINGHOFF

Attesting Officer  Commissioner of Patents and Trademarks